US009869667B2

(12) United States Patent
Blizard et al.

(10) Patent No.: US 9,869,667 B2
(45) Date of Patent: Jan. 16, 2018

(54) SYSTEM AND METHOD FOR CONTROLLING LEARNING PERIOD FOR ADAPTIVE NOISE CANCELLATION

(71) Applicant: Molecular Devices, LLC, Sunnyvale, CA (US)

(72) Inventors: Benjamin Blizard, Oakland, CA (US); Michael Youngquist, Palo Alto, CA (US); Kachoi Tang, San Ramon, CA (US); Krithika Sridhar, Sunnyvale, CA (US)

(73) Assignee: Molecular Devices, LLC, Sunnyvale, CA (US)

( * ) Notice: Subject to any disclaimer, the term of this patent is extended or adjusted under 35 U.S.C. 154(b) by 446 days.

(21) Appl. No.: 14/540,299

(22) Filed: Nov. 13, 2014

(65) Prior Publication Data

US 2016/0142081 A1    May 19, 2016

(51) Int. Cl.
G01N 33/487    (2006.01)
A61B 5/00    (2006.01)

(52) U.S. Cl.
CPC ..... G01N 33/48728 (2013.01); A61B 5/7217 (2013.01); A61B 5/7278 (2013.01)

(58) Field of Classification Search
CPC ................ A61B 5/7217; A61B 5/7278; G01N 33/48728
See application file for complete search history.

(56) References Cited

U.S. PATENT DOCUMENTS

| 3,513,834 | A | * | 5/1970 | Suzuki | ................. | A61B 5/0484 600/544 |
| 4,171,696 | A | * | 10/1979 | John | .................... | A61B 5/0424 600/544 |
| 4,408,616 | A | * | 10/1983 | Duffy | .................. | A61B 5/0484 600/544 |
| 4,539,843 | A | * | 9/1985 | Wise | ....................... | G01C 5/06 73/179 |

(Continued)

FOREIGN PATENT DOCUMENTS

| JP | 02798967 | 9/1998 |
| JP | 2798967 B2 | 9/1998 |

(Continued)

OTHER PUBLICATIONS

Gnecchi et al., "Mirocontrolerbased Biopotential Data Acquisition Systems: Practical Design Considerations", www.intechopen.om, Sep. 2010, 21 pages.*

(Continued)

Primary Examiner — Evan Pert
(74) Attorney, Agent, or Firm — McCracken & Gillen LLC

(57) ABSTRACT

A data acquisition system coupled to a mains power source and a method of operating the data acquisition system are disclosed. A test probe is configured to be coupled to a subject, and an analog to digital converter converts a signal from the test probe to samples. A noise replica generator generates estimates of noise in the samples, and a noise removal block removes from each sample an estimate of noise therein. When the subject is undergoing stimulation, (Continued)

the samples are provided to only the noise removal block. When the subject is not undergoing stimulation, the samples are provided to both the noise replica generator and the noise removal block.

12 Claims, 6 Drawing Sheets

(56) References Cited

U.S. PATENT DOCUMENTS

| | | | | |
|---|---|---|---|---|
| 4,689,759 | A * | 8/1987 | Anouar | H04B 14/04 375/243 |
| 4,744,029 | A * | 5/1988 | Raviv | A61B 5/048 600/544 |
| 4,862,359 | A * | 8/1989 | Trivedi | A61B 5/02755 600/544 |
| 5,139,028 | A * | 8/1992 | Steinhaus | A61B 5/0006 600/508 |
| 5,555,311 | A * | 9/1996 | Reams | H04R 29/004 381/58 |
| 5,611,350 | A * | 3/1997 | John | A61B 5/0484 600/378 |
| 5,699,808 | A * | 12/1997 | John | A61B 5/0484 600/483 |
| 5,916,174 | A | 6/1999 | Dolphin | |
| 5,966,684 | A * | 10/1999 | Richardson | H04B 1/123 702/190 |
| 6,067,467 | A * | 5/2000 | John | A61B 5/0484 600/544 |
| 6,195,576 | B1 * | 2/2001 | John | A61B 5/04008 324/244 |
| 6,321,115 | B1 * | 11/2001 | Mouchawar | A61N 1/37 607/9 |
| 7,072,427 | B2 * | 7/2006 | Rawlins | H03G 3/20 375/345 |
| 8,938,291 | B1 * | 1/2015 | Azarnasab | A61B 5/04017 327/551 |
| 9,294,139 | B1 * | 3/2016 | Blizard | A61B 5/7203 |
| 9,578,432 | B1 * | 2/2017 | Abdollahzadeh Milani | H04R 29/001 |
| 2003/0055609 | A1 * | 3/2003 | Jewett | A61B 5/486 702/189 |
| 2003/0144601 | A1 * | 7/2003 | Prichep | A61B 5/0476 600/544 |
| 2003/0154057 | A1 * | 8/2003 | Jewett | A61B 5/486 702/189 |
| 2004/0064066 | A1 * | 4/2004 | John | A61B 5/04845 600/559 |
| 2004/0079372 | A1 * | 4/2004 | John | A61B 5/048 128/204.18 |
| 2005/0018858 | A1 * | 1/2005 | John | A61B 5/121 381/60 |
| 2006/0094935 | A1 * | 5/2006 | Sussman | A61B 5/16 600/300 |
| 2006/0161218 | A1 * | 7/2006 | Danilov | A61B 5/0492 607/45 |
| 2006/0198533 | A1 * | 9/2006 | Wang | A61B 7/00 381/67 |
| 2007/0202823 | A1 * | 8/2007 | Marsh | H04B 1/1018 455/223 |
| 2008/0200966 | A1 | 8/2008 | Blomberg et al. | |
| 2010/0030096 | A1 * | 2/2010 | Bradley | A61B 5/121 600/544 |
| 2010/0312131 | A1 * | 12/2010 | Naware | A61B 5/0402 600/518 |
| 2012/0065536 | A1 | 3/2012 | Causevic et al. | |
| 2012/0197153 | A1 * | 8/2012 | Kraus | A61B 5/743 600/545 |
| 2014/0086346 | A1 * | 3/2014 | Mottaiyan | H04B 3/30 375/257 |
| 2014/0222382 | A1 | 8/2014 | Patel et al. | |
| 2015/0105837 | A1 * | 4/2015 | Aguilar Domingo | A61N 1/36025 607/45 |
| 2016/0157742 | A1 * | 6/2016 | Huang | A61B 5/7203 600/409 |
| 2016/0278710 | A1 * | 9/2016 | Massie | A61B 5/7203 |

FOREIGN PATENT DOCUMENTS

| | | |
|---|---|---|
| JP | 2011-072725 | 4/2011 |
| JP | 2011072725 A | 4/2011 |
| JP | 2012-055588 | 3/2012 |
| JP | 2012055553 A | 3/2012 |

OTHER PUBLICATIONS

Levkov et al., "Removal of power-line interference from the ECG: a rveiew of the substration procedure", Aug. 2005, BioMedical Engineering OnLine 2005, 4:50, 18 pages.*
Baldwin, Richard G., Adaptive Noise Cancellation using Java, Java Programming Notes # 2360, on developer.com, posted Apr. 18, 2006, http://www.developer.com/java/other/article.php/3599661/Adaptive-Noise-Cancellation-using-Java.htm.
International Search Report and Written Opinion for PCT/IB2015/059224 dated Feb. 16, 2016.

* cited by examiner

SYSTEM AND METHOD FOR CONTROLLING LEARNING PERIOD FOR ADAPTIVE NOISE CANCELLATION

RELATED APPLICATION

This application relates to the US Application entitled: "SYSTEM AND METHOD FOR CONSTRUCTING A NOISE REPLICA" (Docket No.: MDV-0096US) filed on Nov. 13, 2014.

FIELD OF DISCLOSURE

The present subject matter relates to adaptive noise cancellation, and more particularly, to adaptive noise cancellation in an electrophysiology data acquisition system.

BACKGROUND

An electrophysiology data acquisition system is used in biological experiments to monitor and record electrical signals from a subject (e.g., a cell) under test. In such experiments, a researcher may use an experimental rig in which the subject is disposed. The researcher may also secure an electrode or test probe to the subject, for example, using a patch clamp technique, and then analyze the electrical signals detected by the electrode. The electrical signals from the subject may be low-level signals generated by a high-impedance signal source. As a result, such signals may be especially susceptible to electromagnetic interference (EMI) from radiated and conducted emissions of equipment connected to a mains power source. Such EMI may distort the signal of interest and appear as a "noise" or "hum" waveform added to such signal. Further, such noise may be periodic in accordance with the frequency of the electrical current generated by the mains power source. Such frequency is typically 50 hz or 60 hz and low harmonics thereof.

The researcher may use power line conditioners, Faraday cages, avoidance of "ground loops", and the like to isolate the experimental rig from environmental noise sources. Nevertheless, even when great care is taken, EMI may still be introduced in the electrical signal transmitted from the electrode to a data acquisition system. Further, if such electrical signal is affected by EMI at a time in the life cycle of the subject of interest to the researcher, the efforts of the researcher to prepare and isolate the subject may be for naught. Such EMI may result in lost time troubleshooting the experimental apparatus or, worse, in missing the time-window in which live cells must be measured and an irrecoverable loss of the cells.

Typically, an analog electrical signal supplied by the electrode is converted into a stream of digital samples using an analog-to-digital converter. Adaptive noise cancellation techniques may be used to estimate noise components in the stream of digital samples, subtract the estimated noise components from the stream of digital samples, and provide the resulting stream of samples to the researcher.

In some experiments, a passive recording mode may be used in which the system passively records data. In some cases, the system waits for a trigger (for example, from the user) to initiate recording and thereafter passively records data. Other experiments use an episodic stimulation mode in which stimulation is provided to the subject. Such stimulation may include exposing the subject to a chemical or a drug from one or more micro-pipettes, delivering an electrical voltage, exposing the subject to a visible or invisible light source, generating a sound, and the like. The response of the subject reflected in the signal therefrom is simultaneously displayed and/or recorded. Such response is typically displayed in fixed length sweeps. Each sweep is non-overlapping, and an internal timer, a manual pulse or an external pulse may trigger the start of such sweep.

The electrode monitoring the subject may record the stimulation provided to the subject and/or the control signals used to trigger such stimulation. An adaptive noise cancellation unit may erroneously interpret such stimulation signal as noise in the signal from the electrode and attempt to eliminate such erroneous noise from subsequent signals, and thereby corrupt noise-corrected samples generated thereby. The effects of the erroneous noise on the noise-corrected samples may persist for a significant amount of time.

SUMMARY

According to one aspect, a data acquisition system is coupled to a mains power source, and includes a test probe, an analog to digital converter, a noise replica generator, a noise removal block, and a gating module. The test probe is configured to be coupled to a subject, and the analog to digital converter converts a signal from the test probe to samples. The noise replica generator generates estimates of noise in the samples, and the noise removal block that removes from each sample an estimate of noise therein. The gating module determines when the subject is undergoing stimulation. When the subject is undergoing stimulation, the gating module provides the samples to only the noise removal block. When the subject is not undergoing stimulation, the gating module provides the samples to both the noise replica generator and the noise removal block.

According to another aspect, a method of operating a data acquisition system coupled to a mains power source includes the steps of receiving an analog signal from a test probe coupled to a subject. The method further includes the steps of converting the analog signal into samples, operating a noise replica generator that generates estimates of noise in the samples, operating a noise removal block that removes from each sample an estimate of noise therein, and determining when the subject is undergoing stimulation. The samples are provided to only the noise removal block when the subject is undergoing stimulation, and to both the noise replica generator and the noise removal block when the subject is not undergoing stimulation.

DETAILED DESCRIPTION

Figure 1:
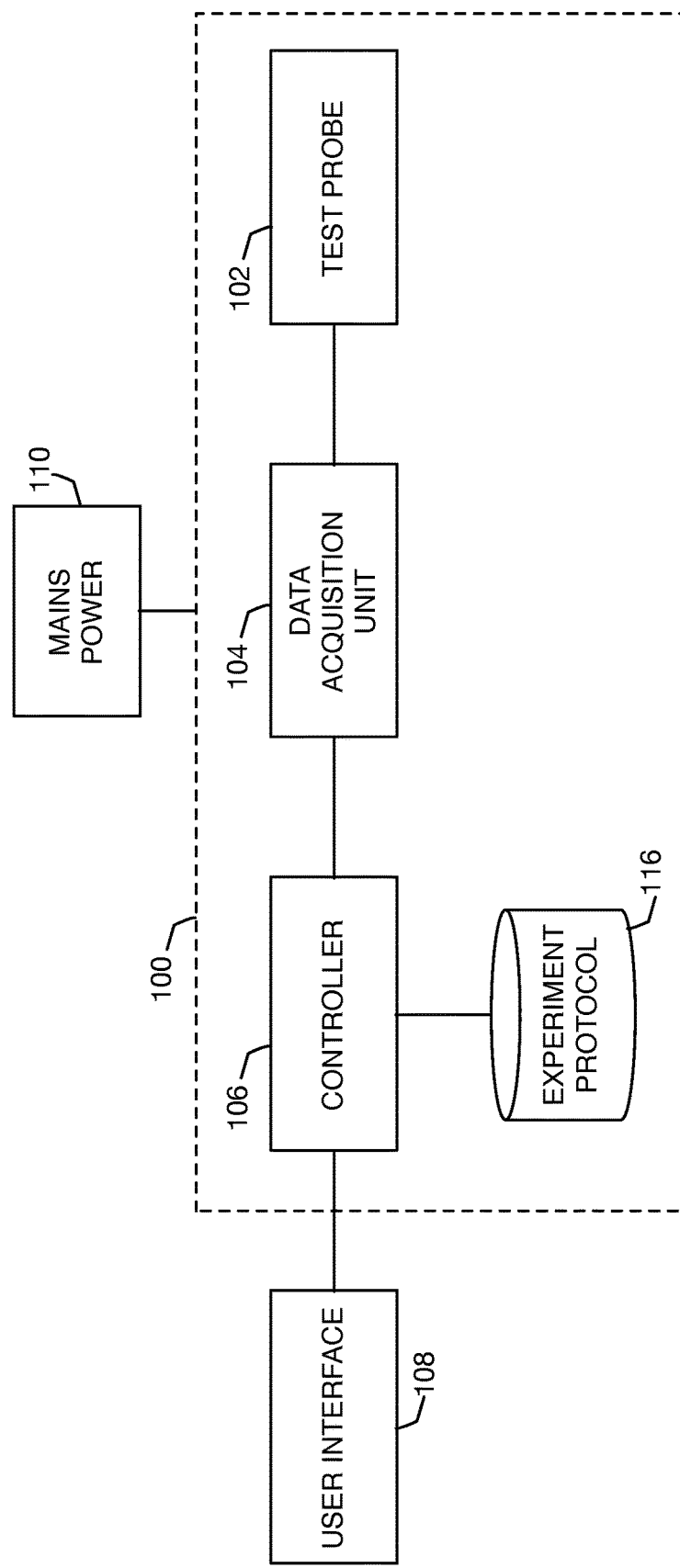
FIG. 1 is a block diagram of a data acquisition system in accordance with the present disclosure.

Referring to FIG. 1, in one embodiment an electrophysiology data acquisition system 100 includes a test probe 102, a data acquisition unit (DAU) 104, and a controller 106. In some embodiments, the system 100 is coupled to a user interface 108 provided, for example, by a computer operated by a user. The DAU 104 and other components of the system 100 may be coupled to a mains power source 110.

Figure 2:
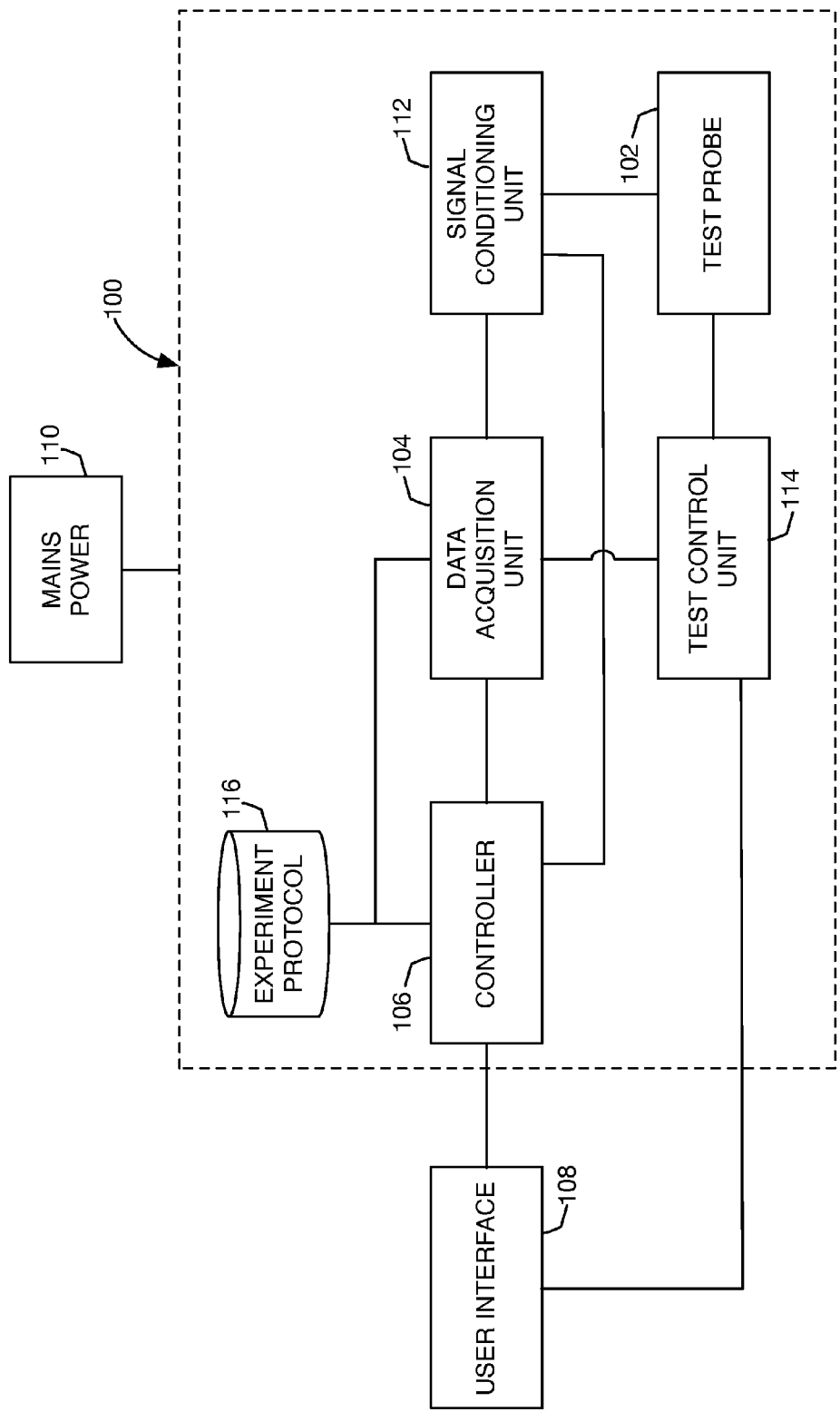
FIG. 2 is a block diagram of another embodiment of the data acquisition system of FIG. 1.

Referring to FIG. 2, in some embodiments the system 100 may further include a signal conditioning unit 112 and/or a test control unit 114. The signal conditioning unit 112 may include for example a passive or active amplifier to amplify the analog signal from the test probe and supply the amplified signal to the DAU 104. In some embodiments, the user may control gain of the amplifier by, for example, operating a knob or a dial, one or more switches, or a slide control disposed on a housing (not shown) in which one or more components of the system 100 are disposed. Alternately, the controller 106 may, for example, control such amplifier electronically, in response to commands received from the user interface 108. In some embodiments, the test probe 102 and the signal conditioning unit 112 may be integrated into a single unit that is electrically coupled to other components of the system 100.

The test probe 102 is electrically coupled to a subject being monitored, and transduces a voltage from the subject and generates an analog signal. The DAU 104 receives the analog signal from the test probe 102, samples the analog signal to generate digital samples of the analog signal, and processes the digital samples to remove noise components therefrom and generates noise corrected output samples. The controller 106 may display such noise corrected output samples on the user interface 108, store such noise corrected output samples on a storage medium (not shown) associated with the system 100, or transmit such noise corrected output samples to another device or system (not shown). The user interface 108 may be directly coupled to the system 100 or may be coupled to the system 100 using a private or public network. Similarly, the storage medium may be directly coupled to the system 100 or may be coupled using a private or public network.

The user operates the user interface 108 to supply to the controller 106 directives to configure the DAU 104 and/or the test probe 102, to initiate sampling of the signals developed by the test probe, and to either store and or display the noise corrected samples. The controller interprets such directives and coordinates the operation of the DAU 104 and/or the test probe 102 accordingly.

If the system 100 is to be used to stimulate the subject and record the response of the subject to such stimulation, as described above, the user may specify when during the stimulation is to be provided, the type of stimulation, the duration of the stimulation, how often the stimulation is to be provided, and the like. The user may supply such experimental protocol information using the user interface 108, or load into the system 100 a file that includes such information. Such a file may be, for example, a text file, an Excel file, an XML file, and the like, that describes the application of a stimulation as a function of time. In one embodiment, the file may be in accordance with the Axon Binary Format specified by Molecular Devices LLC of Sunnyvale, Calif. The controller 106 receives and stores the experimental protocol information an experiment protocol database 116.

In some embodiments, the system 100 may coordinate the operation of test control unit 114 to stimulate the subject being monitored as specified in the experiment protocol database 116. In some embodiments, the user interface 108 may directly control the test control unit 114. In other embodiments, the system 100 may receive directives from the user interface 108 regarding the stimulation to be provided, and the system 100 actuates the test control unit 114 accordingly. In some embodiments, if the user interface 108 directly controls the test control unit 114 to provide stimulation to the subject, the user interface 108 notifies the controller 106 regarding characteristics of such stimulation, and the controller 106 records such characteristics in the experimental protocol database 116.

Figure 3:
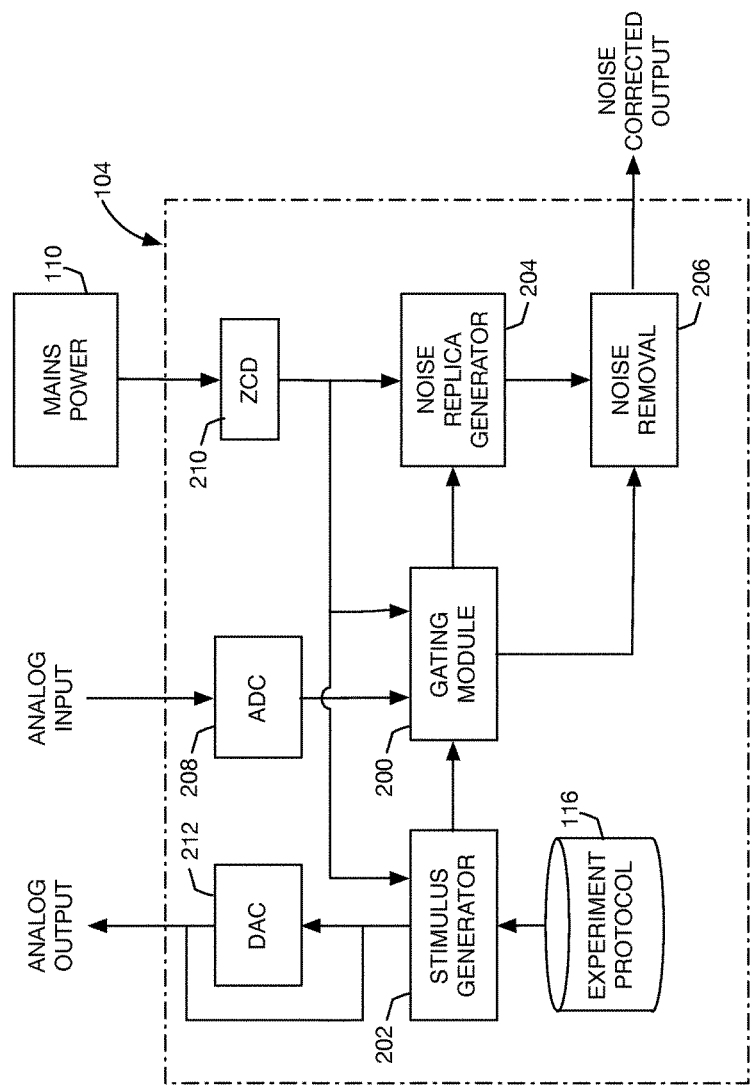
FIG. 3 is a block diagram of a data acquisition unit of the data acquisition system of FIG. 1.

Referring to FIG. 3, an embodiment of the DAU 104 includes a gating module 200, a stimulus generator 202, a noise replica generator 204, and a noise removal module 206. The gating module 200 receives from an analog-to-digital converter (ADC) 208 a stream of samples of an analog signal from the test probe 102. The gating module 200 may supply the stream of samples to the noise replica generator 204 and the noise removal module 206. The noise replica generator 204 develops an estimate of the noise component in each sample of the stream of samples, and supplies such estimate to the noise removal module 206. The noise removal module 206 subtracts the noise estimate 204 generated by the noise replica generator 204 from a corresponding sample from the corresponding sample from the gating module 200. The result is generated as a noise corrected output of the DAU 104.

The DAU 104 also includes a zero-crossing detector 210 that monitors the voltage supplied by the mains power source 110 and generates a zero-crossing signal in accordance with the frequency of such voltage. It should be apparent to those who have skill in the art that a debounce filter or circuit may condition the signal from the mains power source 110 and the ZCD 210 monitors the voltage in such conditioned signal. In some embodiments, if the DAU 104 is operated in the United States, the ZCD 210 generates a zero-crossing signal 120 times-per-second in accordance with the 60 Hz power line frequency used in the United States. Similarly, if the DAU 104 is operated in Europe, the ZCD 204 may generate a zero-crossing signal 100 times-per-second in accordance with 50 Hz power line used there. In other embodiments, the ZCD 204 may generate the zero-crossing signal only in response to a positive to negative voltage transition in the mains power source 110, and therefore, generates the zero-crossing signal either 60 times-per-second in the United States and 50 times-per-second in Europe. Alternately, the ZCD 204 may generate the zero-crossing signal only in response to a negative to positive voltage transition in the mains power source 110. Other ways of developing the zero-crossing signal apparent to those who have skill in the art may be used. As should be apparent to those who have skill in the art, the zero-crossing signal generated by the ZCD 210 delimits each periodic cycle of the mains power source.

In one embodiment, the ZCD 204 includes an analog to digital converter (not shown) that samples power line supplied by the mains power source 110, and analyzes that waveform represented by such samples to find the zero crossing. In another embodiment, the ZCD 204 may determine the zero crossing using a transformer and a comparator, or an optocoupler and comparator, as would be apparent to those who have skill in the art. Other ways of developing the zero-crossing signal apparent to those who have skill in the art may be used.

Although zero-crossing signal generated by the ZCD 204 described represents a time when the voltage of the power line is zero, one of skill in the art should understand the zero-crossing signal may be generated when the power line is at any predefined voltage that indicates a start of a cycle of periodic waveform associated with the power line. The zero-crossing signal indicates any consistent position of such waveform. For example, a zero-crossing signal may be generated at 0.2476 volts in the positive going direction or 88.32 V in the negative going direction or any other value that is reached or crossed during each cycle of the mains. The zero-crossing signal generated by the ZCD 204 may be any signal that can be used to synchronize the phase of the components of the noise replica generator 200 to that of the mains power source 110. As such, the zero-crossing signal generated by the ZCD 204 is a mains cycle start signal.

The gating module 200 and the noise replica generator 204 synchronize the operations thereof with the zero-crossing signal developed the ZCD 210, so that the sample received by the noise removal module 206 is temporally aligned with a corresponding noise estimate generated by the noise replica generator 204. In this manner, the system 100 may be used without modification in different countries having mains sources that supply power at different frequencies.

If the DAU 104 is operated to monitor response of the subject exposed to stimulation, the stimulation generator 202 queries the experiment protocol database 116 for information regarding such stimulation. When the stimulation is to be supplied to the subject, the stimulus generator 202 supplies a gating signal to the gating module 200 that indicates the subject will undergo stimulation. In response, the gating module 200 stops supplying the samples generated by the ADC 208 to the noise replica generator 204, so that samples that may include stimulation signals are not included in the noise estimates developed by the noise replica generator 204.

In some embodiments, the stimulus generator 202 also monitors the zero-crossing detection signal, and develops the gating signal during the periodic cycle that just precedes the periodic cycle of the mains power source 110 during which the stimulation will be supplied to the subject. Thus, in such embodiments, the gating signal generated by the stimulus generator 202 alerts the gating module 200 that the stimulus will be applied in the next periodic cycle of the mains power source 110 as indicated by the zero-crossing signal. In response, the gating module 200 does not supply any samples generated by the ADC 208 to the noise replica generator 204 during such periodic cycle.

In some embodiments, the stimulus generator 202 generates separate gating signals that indicated initiation of stimulation of the subject and cessation of such stimulation. In some cases, the cessation signal may be generated during the periodic cycle of the mains source 110 in which the stimulation will be stopped.

In some embodiments, if stimulation that is provided to the subject spans multiple periodic cycles of the mains power source 110, the stimulus generator 202 generates a gating signal prior to each such periodic cycle.

In some embodiments, the stimulus generator 202 determines from the experimental protocol database 116 the type of stimulation that is to be supplied to the subject, and generates an analog signal to control the test control unit 114 or other apparatus coupled to the DAU 104 to deliver such stimulation. In other embodiments, the stimulus generator 202 generates a digital signal that is converted into an analog signal by a digital-to-analog converter (DAC) 212, and such analog signal is provided to the test control unit 114 or other apparatus. In still other embodiments, the stimulus generator 202 generates a digital command stream or signal that is supplied to the test control unit 114 or other apparatus.

Figure 4:
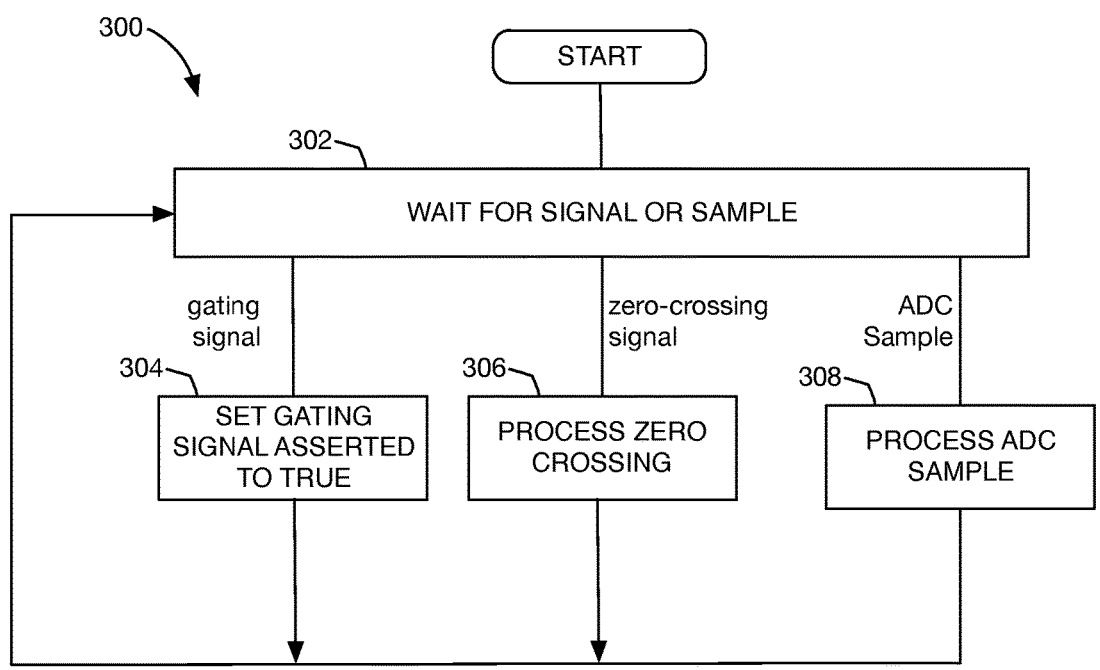
FIG. 4 is diagram of a state machine to illustrate the operation of a gating module of the data acquisition unit of FIG. 3.

Referring to FIG. 4, in one embodiment the gating module 200 may operate as a state machine 300. When started, the gating module 200 enters a wait state 302 in which the gating module 200 waits for either the gating or the zero-crossing signal to be generated by the stimulus generator 202 or the ZCD 210, respectively, or for a sample to be generated by the ADC 208.

While in the wait state 302, if the gating module 200 receives the gating signal from the stimulus generator 202, the gating module 200 transitions to a state 304, in which the gating module 200 sets the value of a gating signal asserted flag to true, and returns to the wait state 302.

If, while in the wait state 302, the gating module 200 receives a zero-crossing signal from the ZCD 210, the gating module 200 transition to a process zero crossing state 306 to processes the zero crossing signal. Thereafter, the gating module 200 returns to the wait state 302.

If, while in the wait state 302, the gating module 200 receives a sample from the ADC 208, the gating module 200 transitions into a process ADC sample state 308. Thereafter, the gating module 200 returns to the wait state 302.

Figure 5:
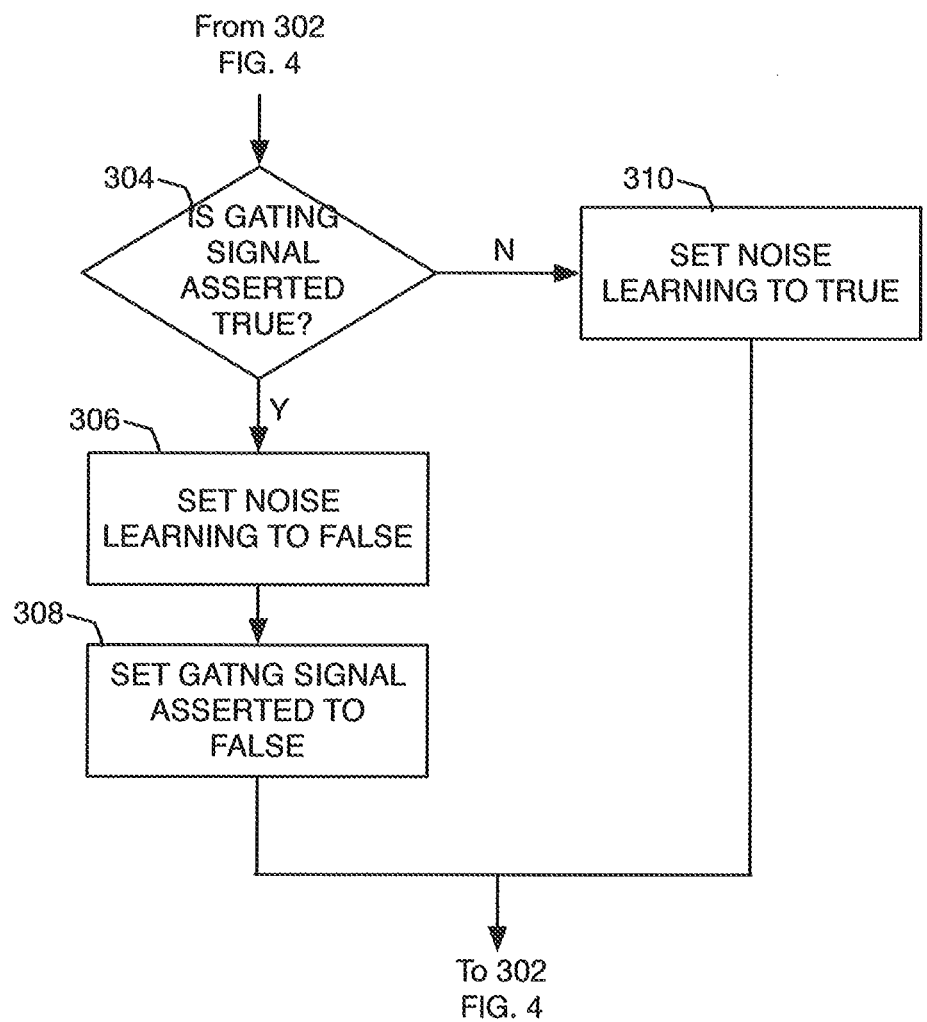
FIG. 5 is a flowchart of processing undertaken during a process zero crossing state of the state machine of FIG. 4.

Referring to FIG. 5, when in the process zero crossing state 306, the gating module 200 determines, at block 304, if the gating signal asserted flag is true. If so, the gating module 200, at block 306, sets a noise learning flag to false off, and sets the gating signal asserted flag to false, at block 308. The gating module 200 then returns to the wait state 302 (FIG. 4).

However, if the gating module 200, at block 304, determines the gating signal asserted flag is off, the gating module 200 sets the noise learning flag to true, at block 310. The gating module 200 then returns to the wait state 302 (FIG. 4).

Figure 6:
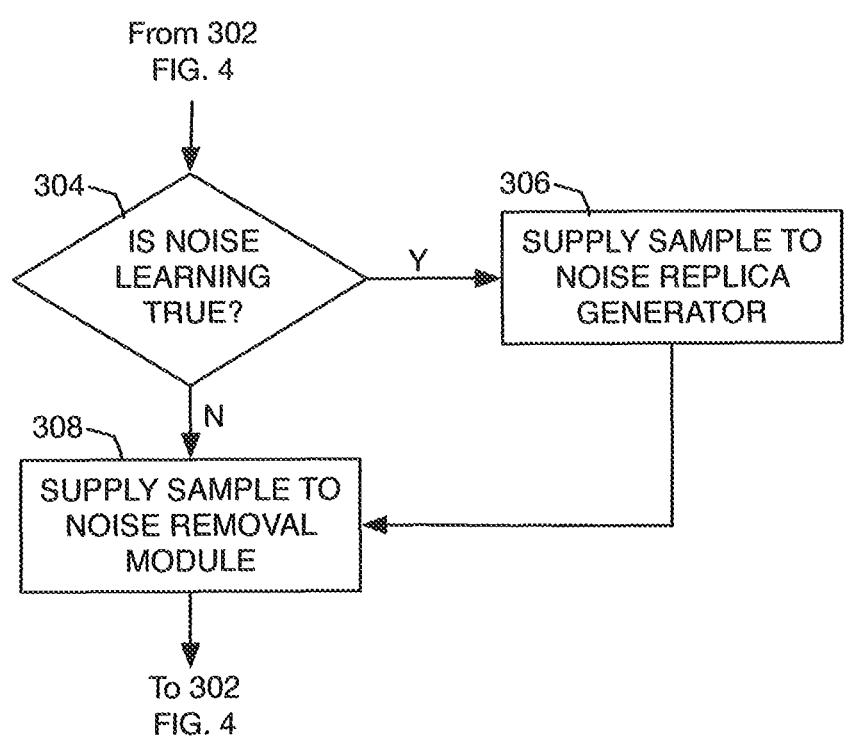
FIG. 6 is a flowchart of processing undertaken during a process ADC sample state of the state machine of FIG. 4.

Referring to FIG. 6, when in the process ADC sample state 308, the gating module 200 at block 304 determines if the noise learning flag is true. If so, the gating module 200 proceeds to block 306. Otherwise, the gating module 200 proceeds to block 308. At block 306 the gating module 200 supplies the received sample to the noise replica generator 204 and proceeds to block 308.

At block 308 the gating module 200 supplies the received sample to the noise removal module 206. After block 308, the gating module 200 returns to the wait state 302 (FIG. 4).

In one embodiment the noise replica generator 204 generates a noise estimate each time the ADC 208 generates a sample. Such noise estimate is generated even if the noise replica generator 204 does not receive a sample from the gating module 200. During periods when the noise replica generator 204 does not receive new samples generated by the ADC 208, the noise replica generator 204 generates noise estimates based on previously received samples. The noise replica generator 204 may be any noise replica generator that uses a controllable learning period.

As described above, operation of the stimulus generator 202, gating module 200, and the noise replica generator 204 are synchronized using the zero-crossing signal generated by the ZCD 210. Such synchronization allows that gating module 200 to determine particular periods of time (i.e., one or more periodic cycles of the mains power source 110) during which the noise replica generator 204 should not update internal estimates of noise in the analog input.

It should be apparent to those who have skill in the art that any combination of hardware and/or software may be used to implement the noise removal processing system described herein. It will be understood and appreciated that one or more of the processes, sub-processes, and process steps described in connection with FIGS. 1-6 may be performed by hardware, software, or a combination of hardware and software on one or more electronic or digitally-controlled devices. The software may reside in a software memory (not shown) in a suitable electronic processing component or system such as, for example, one or more of the functional systems, controllers, devices, components, modules, or sub-modules schematically depicted in FIGS. 1-6. The software memory may include an ordered listing of executable instructions for implementing logical functions (that is, "logic" that may be implemented in digital form such as digital circuitry or source code, or in analog form such as analog source such as an analog electrical, sound, or video signal). The instructions may be executed within a processing module or controller (e.g., the gating module 200, the Noise Replica Generator 204, the Noise Removal Block 206, the ADC unit 208, the Zero Crossing Detector 210, and the DAC 212 of FIG. 3), which includes, for example, one or more microprocessors, general purpose processors, combinations of processors, digital signal processors (DSPs), field programmable gate arrays (FPGAs), or application-specific integrated circuits (ASICs). Further, the schematic diagrams describe a logical division of functions having physical (hardware and/or software) implementations that are not limited by architecture or the physical layout of the functions. The example systems described in this application may be implemented in a variety of configurations and operate as hardware/software components in a single hardware/software unit, or in separate hardware/software units.

The executable instructions may be implemented as a computer program product having instructions stored therein which, when executed by a processing module of an electronic system, direct the electronic system to carry out the instructions. The computer program product may be selectively embodied in any non-transitory computer-readable storage medium for use by or in connection with an instruction execution system, apparatus, or device, such as an electronic computer-based system, processor-containing system, or other system that may selectively fetch the instructions from the instruction execution system, apparatus, or device and execute the instructions. In the context of this document, computer-readable storage medium is any non-transitory means that may store the program for use by or in connection with the instruction execution system, apparatus, or device. The non-transitory computer-readable storage medium may selectively be, for example, an electronic, magnetic, optical, electromagnetic, infrared, or semiconductor system, apparatus, or device. A non-exhaustive list of more specific examples of non-transitory computer readable media include: an electrical connection having one or more wires (electronic); a portable computer diskette (magnetic); a random access, i.e., volatile, memory (electronic); a read-only memory (electronic); an erasable programmable read only memory such as, for example, Flash memory (electronic); a compact disc memory such as, for example, CD-ROM, CD-R, CD-RW (optical); and digital versatile disc memory, i.e., DVD (optical).

It will also be understood that receiving and transmitting of signals as used in this document means that two or more systems, devices, components, modules, or sub-modules are capable of communicating with each other via signals that travel over some type of signal path. The signals may be communication, power, data, or energy signals, which may communicate information, power, or energy from a first system, device, component, module, or sub-module to a second system, device, component, module, or sub-module along a signal path between the first and second system, device, component, module, or sub-module. The signal paths may include physical, electrical, magnetic, electromagnetic, electrochemical, optical, wired, or wireless connections. The signal paths may also include additional systems, devices, components, modules, or sub-modules between the first and second system, device, component, module, or sub-module.

INDUSTRIAL APPLICABILITY

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar references in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the disclosure and does not pose a limitation on the scope of the disclosure unless otherwise claimed. No language in the specification should be construed as indicating any non-claimed element as essential to the practice of the disclosure.

Numerous modifications to the present disclosure will be apparent to those skilled in the art in view of the foregoing description. It should be understood that the illustrated embodiments are exemplary only, and should not be taken as limiting the scope of the disclosure.

We claim:

1. A data acquisition system coupled to a mains power source that provides cyclical periods of power, comprising:
    a test probe configured to be coupled to a subject;
    an analog to digital converter that converts a signal from the test probe to samples;
    a noise replica generator that generates estimates of noise in the samples;
    a noise removal block that removes from each sample an estimate of noise therein;
    a period detector that detects starts of first and second cyclical periods of the power provided by the mains power source and generates a signal indicating each such start, wherein the second cyclical period precedes the first cyclical period;
    a stimulus generator that monitors the signal generated by the period detector and applies stimulation to the subject during the first cyclical period of the power, does not apply stimulation to the sample during the second cyclical period of power, and generates a gating signal during the second cyclical period of the power; and
    a gating module that monitors the gating signal and determines when the subject is undergoing stimulation, wherein the gating module provides the samples to the noise removal block and not to the noise replica generator when the subject is undergoing stimulation, and provides samples to both the noise replica generator and the noise removal block when the subject is not undergoing stimulation.

2. The data acquisition system of claim 1, wherein the gating module does not provide any samples to the noise replica generator during the cyclical period during which stimulation is to be applied.

3. The data acquisition system of claim 1, wherein the stimulus generator provides an indication to the gating module that the subject will undergo stimulation prior to each of a plurality of cyclical periods during which stimulation is applied to the subject.

4. The data acquisition system of claim 1, wherein the stimulus generator provides an indication the stimulation is to cease during a third cyclical period.

5. The data acquisition system of claim 1, wherein the stimulus generator causes the stimulation to be provided to the subject.

6. The data acquisition system of claim 1, wherein the subject is a biological sample.

7. A method of operating a data acquisition system coupled to a mains power source, wherein the mains power source provides cyclical periods of power, comprising:
receiving an analog signal from a test probe coupled to a subject;
converting the analog signal into samples;
operating a noise replica generator that generates estimates of noise in the samples;
operating a noise removal block that removes from each sample an estimate of noise therein;
detecting starts of first and second cyclical periods of power provided by the mains power source, wherein the second cyclical pried precedes the first cyclical period;
applying stimulation to the subject during the first cyclical period and not applying stimulation to the subject during the second cyclical period;
generating a gating signal during the second cyclical period; and
monitoring the gating signal to determine when the subject is undergoing stimulation and providing the samples to the noise removal block and not the noise replica generator when the subject is undergoing stimulation, and providing the samples to both the noise replica generator and the noise removal block when the subject is not undergoing stimulation.

8. The method of claim 7, further including generating a signal that the subject will undergo stimulation prior to each of a plurality of cyclical periods during which stimulation is applied to the subject.

9. The method of claim 8, wherein no samples are provided to the noise replica generator during the cyclical period during which stimulation is to be applied.

10. The method of claim 9, further including generating a signal that stimulation will be applied to the subject during a third cyclical period and another signal that the stimulation is to cease during a fourth cyclical period.

11. The method of claim 9, further including causing stimulation to be provided to the subject.

12. The method of claim 7, further including coupling the test probe to a subject that is a biological sample.

* * * * *